United States Patent [19]  [11] Patent Number: 4,537,895
Deák et al.  [45] Date of Patent: Aug. 27, 1985

[54] ISOQUINOLINE DERIVATIVES

[75] Inventors: Gyula Deák; Erzsébet Zára née Kaczián; Lajos György; Márton Fekete; Margit Dóda; András Seregi, all of Budapest; Béla Kanyicska, Kerepestarcsa; Erzsébet Tóth née Pécsi, Budapest; Mária Horváth née Gaál, Budapest; Sándor Mányai, Budapest; Frigyes Görgényi, Budapest; Györgyi Vászovics née Reichmann, Budapest, all of Hungary

[73] Assignee: EGYT Gyógyszervegyészeti Gyár, Budapest, Hungary

[21] Appl. No.: 500,969

[22] Filed: Jun. 3, 1983

[30] Foreign Application Priority Data

Apr. 4, 1982 [HU] Hungary ..................... 1797
Apr. 4, 1982 [HU] Hungary ..................... 1798
Apr. 4, 1982 [HU] Hungary ..................... 1799

[51] Int. Cl.³ ..................... A61K 31/47; C07D 217/04
[52] U.S. Cl. ..................... 514/307; 514/222; 514/234; 514/253; 514/58.6; 514/128; 514/363
[58] Field of Search ............... 546/143; 544/128, 363, 544/58.6; 424/250, 248.54, 258

[56] References Cited

U.S. PATENT DOCUMENTS 3,674,791  7/1972  Mathison .................... 546/143
3,886,166  5/1975  Casagrande et al. ........ 546/143
3,910,915  10/1975 Yonan ....................... 544/363
4,185,105  1/1980  Schmitt et al. ............. 546/143

FOREIGN PATENT DOCUMENTS 1153471  5/1969  United Kingdom .......... 544/263

OTHER PUBLICATIONS

Hoechst, "Chemical Abstracts", vol. 72, 1970, col. 21621e.
Eiden et al., "Chemical Abstracts", vol. 87, 1977, col. 87:102137p.

Primary Examiner—Glennon H. Hollrah

Assistant Examiner—James H. Turnipseed
Attorney, Agent, or Firm—Keil & Weinkauf

[57] ABSTRACT

The invention relates to new 4-aryl-2-methyl-1,2,3,4-tetrahydro-isoquinoline derivatives of the general Formula I

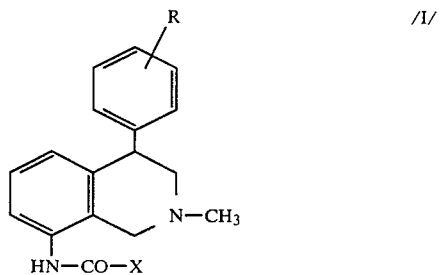

and salts thereof
wherein
R stands for hydrogen, lower alkyl or halogen and
X represents a group of the general Formula —(CH$_2$)$_n$—NR$^1$R$^2$, —NH—R$^3$ or —OR$^4$, in which
R$^1$ and R$^2$ may be the same or different and stand for hydrogen or lower alkyl or R$^1$ and R$^2$ together with the adjacent nitrogen atom, they are attached to, form a 5- or 6-membered saturated heterocyclic ring which may optionally contain a further oxygen or sulfur atom or an optionally lower alkyl substituted imino group;
n is an integral number 1, 2, 3 or 4;
R$^3$ stands for lower alkyl or optionally substituted phenyl and
R$^4$ is lower alkyl, halogeno lower alkyl, or phenyl lower alkyl.

The compounds of the general Formula I are useful as antidepressants and antiparkinsone agents.

The compounds of the general Formula I can be prepared by methods known per se.

9 Claims, No Drawings

ISOQUINOLINE DERIVATIVES

This invention relates to new 4-aryl-2-methyl-1,2,3,4-tetrahydro-isoquinoline derivatives, a process for the preparation thereof and pharmaceutical compositions containing the same.

8-Amino-4-aryl-2-alkyl-tetrahydro-isoquinoline derivatives substituted on the amino group by an acyl group derived from a saturated or unsaturated aliphatic carboxylic acid containing not more than 6 carbon atoms, an aromatic carboxylic acid or an arylaliphatic carboxylic acid containing 7-10 carbon atoms are described in British Patent Specification No. 1,164,192. These compounds exhibit central nervous system stimulating and tymoleptic effect. Compounds of similar structure are disclosed in DOS No. 1,670,848 and 1,795,829.

According to a feature of the present invention there are provided new 4-aryl-2-methyl-1,2,3,4-tetrahydro-isoquinoline derivatives of the general Formula I

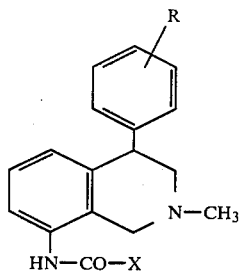

/I/ and pharmaceutically acceptable acid addition salts thereof
wherein,
R stands for hydrogen, lower alkyl or halogen and
X represents a group of the general Formula $-(CH_2)_n-NR^1R^2$, $-NH-R^3$ or $-OR^4$, in which
  $R^1$ and $R^2$ may be the same or different and stand for hydrogen or lower alkyl or $R^1$ and $R^2$ together with the adjacent nitrogen atom, they are attached to, form a 5- or 6-membered saturated heterocyclic ring which may optionally contain a further oxygen or sulfur atom or an optionally lower alkyl substituted imino group;
  n is an integral number 1, 2, 3 or 4;
  $R^3$ stands for lower alkyl or optionally substituted phenyl and
  $R^4$ is lower alkyl, halogeno lower alkyl or phenyl lower alkyl.

A preferred sub-group of the compounds of the general Formula I corresponds to the general Formula IA

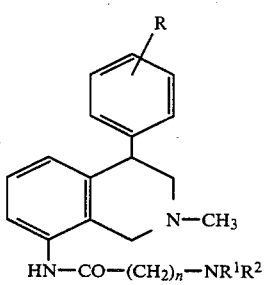

IA wherein R, $R^1$, $R^2$ and n are as stated above.

Preferred representatives of the compounds of the general Formula IA are the following compounds:
8-ethylamino-acetylamino-4-p-chloro-phenyl-2-methyl-1,2,3,4-tetrahydro-isoquinoline;
8-n-butylamino-acetylamino-4-p-chloro-phenyl-2-methyl-1,2,3,4-tetrahydro-isoquinoline;
8-ethylamino-acetylamino-4-p-tolyl-2-methyl-1,2,3,4-tetrahydro-isoquinoline;
8-n-butylamino-acetylamino-4-p-tolyl-2-methyl-1,2,3,4-tetrahydro-isoquinoline;
and pharmaceutically acceptable acid addition salts thereof.

A further preferred sub-group of the compounds of the general Formula I corresponds to the general Formula IB

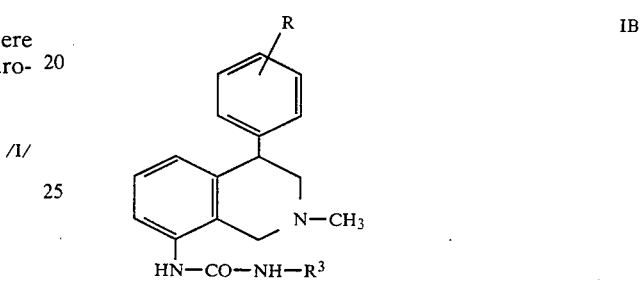

IB wherein R and $R^3$ are as stated above.

Preferred representatives of the compounds of the general Formula IB are the following derivatives:
8-n-butyl-carbamoylamino-4-p-chloro-phenyl-2-methyl-1,2,3,4-tetrahydro-isoquinoline;
8-n-butyl-carbamoylamino-4-p-tolyl-2-methyl-1,2,3,4-tetrahydro-isoquinoline;
and pharmaceutically acceptable acid addition salts thereof.

A still further preferred sub-group of the compounds of the general Formula I corresponds to the general Formula IC

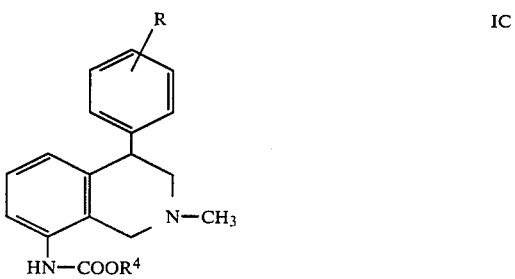

IC wherein R and $R^4$ are as stated above.

A preferred representative of the compounds of the general Formula IC is the 8-ethoxycarbonylamino-4-p-chloro-phenyl-2-methyl-1,2,3,4-tetrahydro-isoquinoline and pharmaceutically acceptable acid addition salts, particularly the hydrochloride thereof. This compound and its salts possess particularly advantageous therapeutical properties.

The term "lower alkyl" used throughout the specification relates to straight or branched chain aliphatic groups having 1-6, particularly 1-4 carbon atoms (e.g. methyl, ethyl, n-propyl, isopropyl, n-butyl, isobutyl etc). The term "halogen" encompasses the fluorine, chlorine, bromine and iodine atoms. The 5- or 6-membered saturated heterocyclic ring formed by $R^1$, $R^2$ and the adjacent nitrogen atom, they are attached to, can be e.g. pyrrolidino, piperidino, morpholino, thiomorpholino, piperazino or N-substituted piperazino e.g. N-alkyl- or N-benzyl-piperazino, such as N-methylpiperazino. Symbol n is preferably 1 or 2. The substituent R is attached preferably to the para-position of the phenyl ring.

$R^3$ as optionally substituted phenyl may bear one or more identical or different substituents, such as halogen (e.g. chlorine, bromine, iodine) and/or alkyl (e.g. methyl, ethyl etc.).

The pharmaceutically acceptable acid addition salts of the compounds of the general Formula I can be formed with pharmaceutically acceptable inorganic or organic acids. Thus the salts may be formed with mineral acids (e.g. hydrogen halides, such as hydrochlorides, hydrobromides, sulfates, phosphates etc.) or organic acids (such as formiates, acetates, propionates, lactates, maleates, tartarates, benzoates, salicylates etc.).

According to a further feature of the present invention there is provided a process for the preparation of compounds of the general Formula I
wherein
R stands for hydrogen, lower alkyl or halogen and
X represents a group of the general Formula —$CH_2$. )$_n$——$NR^1R^2$, —NH—$R^3$ or —$OR^4$, in which
  $R^1$ and $R^2$ may be the same or different and stand for hydrogen or lower alkyl or $R^1$ and $R^2$ together with the adjacent nitrogen atom, they are attached to, form a 5- or 6-membered saturated heterocyclic ring which may optionally contain a further oxygen or sulfur atom or an optionally lower alkyl substituted imino group;
  n is an integral number 1, 2, 3 or 4;
  $R^3$ stands for lower alkyl or optionally substituted phenyl and
  $R^4$ is lower alkyl, halogeno lower alkyl, or phenyl lower alkyl
and pharmaceutically acceptable acid addition salts thereof, which comprises
(a) for the preparation of compounds of the general Formula IA (wherein R, $R^1$, $R^2$ and n are as stated above), reacting a compound of the general Formula II

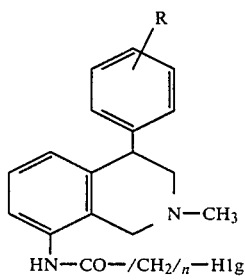

wherein Hlg is halogen and R and n are as stated above or a salt thereof with an amine of the general Formula III $NHR^1R^2$     III wherein $R^1$ and $R^2$ are as stated above or a salt thereof; or
(b) for the preparation of compounds of the general Formula IB wherein R and $R^3$ are as stated above, (b$_1$) reacting a compound of the general Formula IV

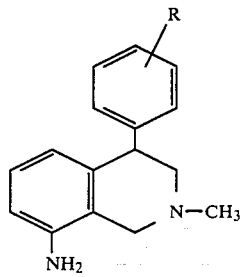

wherein R is as stated above with an isocyanate of the general Formula V $R^3$—NCO     V wherein $R^3$ is as stated above, or
(b$_2$) subjecting a compound of the general Formula VI

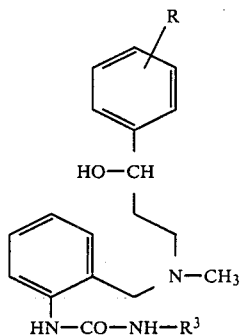

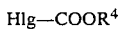

wherein R and $R^3$ are as stated above to cyclisation); or
(c) for the preparation of compounds of the general Formula IC, wherein R and $R^4$ are as stated above,
(c$_1$) reacting a compound of the general Formula IV wherein R is as stated above with a halogeno formiate of the general Formula VII Hlg—$COOR^4$     VII wherein Hlg is halogen, preferably chlorine or bromine and $R^4$ is as stated above; or
(c$_2$) subjecting a compound of the general Formula VIII

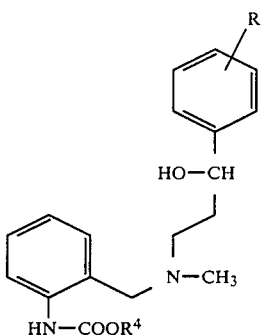

wherein R and $R^4$ are as stated above to ring-closure, and, if desired, converting a compound of the general Formula I into a pharmaceutically acceptable acid addition salt thereof.

According to process (a) of the present invention a compound of the general Formula II or a salt thereof is reacted with an amine of the general Formula III or a salt thereof. The said reaction can be preferably carried out in an inert organic solvent. As reaction medium preferably aliphatic alcohols, particularly methanol or ethanol, can be used. The reaction may be carried out at elevated temperature, preferably at the boiling point of the reaction mixture.

The starting materials of the general Formulae II and III can also be used in the form of their acid addition salts (e.g. hydrochlorides).

The reaction mixture can be worked up by methods known per se. Thus one may proceed by distilling off the solvent and isolating the product by extraction with an organic solvent.

The starting materials of the general Formula II can be prepared from the compounds of the general Formula XI

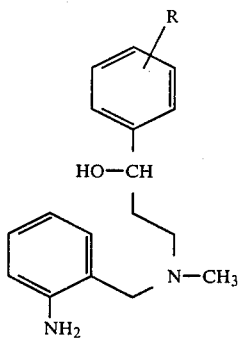

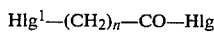

wherein R is as stated above by two methods:

According to the first method a compound of the general Formula XI is subjected to ring-closure and the compound of the general Formula IV thus obtained is reacted with an acid halide of the general Formula X $$Hlg^1-(CH_2)_n-CO-Hlg \qquad X$$

wherein Hlg is as stated above, and $Hlg^1$ stands for halogen, preferably chlorine.

The cyclisation of the compounds of the general Formula XI is carried out in an inert organic solvent. As reaction medium halogenated hydrocarbons e.g. methylene chloride, chloroform etc. can be used. The reaction may be accomplished in the presence of an acidic catalyst. For this purpose mineral acids (e.g. sulfuric acid, polyphosphoric acid or polyphosphate esters etc.) can be used. The reaction takes already place at lower temperature, e.g. at 0°–5° C.

The reaction of the compound of the general Formula IV thus obtained and the ω-halogeno-acid chloride of the general Formula X can be carried out in an inert organic solvent. As reaction medium preferably aromatic hydrocarbons (e.g. benzene, toluene, xylene etc.) can be used. The reaction may be advantageously carried out at an elevated temperature, preferably at the boiling point of the reaction mixture. The reaction can be accomplished in the presence of an acid binding agent (e.g. a tertiary organic base, such as triethyl amine, quinoline etc.).

The compound of the general Formula II can be isolated from the reaction mixture by known methods (e.g. filtration, crystallization etc.).

The crude compounds of the general Formula II can be directly used for the preparation of the compounds of the general Formula I without purification.

According a further method the starting materials of the general Formula II can be prepared by reacting a compound of the general Formula XI with a ω-halogeno-acid halide of the general Formula X and subjecting the compound of the general Formula IX

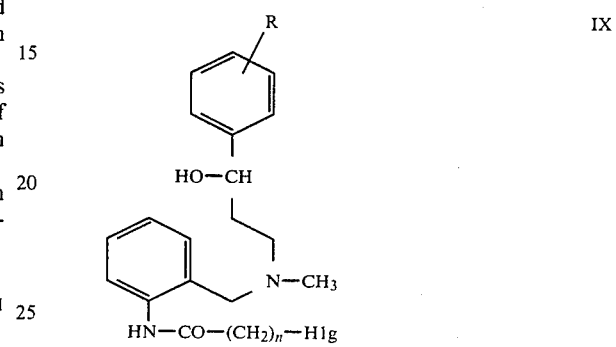

thus obtained wherein R, Hlg and n are as stated above to ring-closure.

The reaction of the compounds of the general Formulae XI and X can be carried out in an analogous manner to the reaction of the compounds of the general Formulae IV and X. The cyclication of the compound of the general Formula IX can be accomplished in an analogous manner to the ring-closure of the compounds of the general Formula XI.

The compounds of the general Formulae IV and XI are either known (British patent specification No. 1,164,192) or can be prepared by known methods.

According to process ($b_1$) of the present invention a compound of the general Formula IV is reacted with an isocyanate of the general Formula V. The reaction is carried out in an inert organic solvent. As reaction medium preferably aromatic hydrocarbons may be used (e.g. benzene, toluene, xylene etc.).

The reaction may be carried out under heating, preferably at the boiling point of the reaction mixture.

The reaction mixture can be worked up by methods known per se. Thus one may proceed by evaporating the solvent and purifying the residue by chromatographical methods.

The starting materials of the general Formula IV can be prepared by cyclisation of the compounds of the general Formula XI.

According to process ($b_2$) a compound of the general Formula VI is subjected to ring-closure. The cyclisation is carried out in the presence of an acidic catalyst. For this purpose mineral acids (e.g. sulfuric acid, polyphosphoric acid etc.) or Lewis acids (e.g. boron trifluoride, aluminium chloride, zinc chloride, tin chloride etc.) can be used. Sulfuric acid is a particularly useful acidic catalyst. The reaction is carried out in an organic solvent, preferably halogenated hydrocarbons (e.g. methylene chloride, chloroform etc.). The reaction temperature depends on the activity of the catalyst. If sulfuric acid is used as catalyst, the reaction takes rapidly place already at lower temperature, e.g. at 0°–6° C.

The reaction mixture can be worked up by methods known per se. If sulfuric acid is used as catalyst, the acidic reaction mixture is poured onto ice, the mixture is made alkaline and the product is isolated by extraction. As extracting agent preferably halogenated hydrocarbons (e.g. chloroform) can be used.

The starting materials of the general Formula VI can be prepared by reacting a compound of the general Formula XI with an isocyanate of the general Formula V. This reaction is carried out in an analogous manner to process $b_1$ of the present invention.

According to process ($c_1$) of the present invention a compound of the general Formula IV is reacted with a halogeno formiate of the general Formula VII. It is preferred to use compounds of the general Formula VII in which Hlg is chlorine. The reaction is carried out in an inert organic solvent. As reaction medium preferably aromatic hydro-carbons (e.g. benzene, toluene, xylene etc.) can be used. The reaction may be preferably accomplished at elevated temperature, particularly at the boiling point of the reaction mixture. The reaction may also be effected in the absence of a solvent. The reaction may be preferably carried out in the presence of an acid binding agent, such as tertiary amines, e.g. triethyl amine or quinoline.

The reaction mixture may be worked up by methods known per se. Thus one may proceed by evaporating the reaction mixture, making the residue alkaline (e.g. with ammonium hydroxide) and extracting the desired compound of the general Formula I with an organic solvent (e.g. chloroform).

The compounds of the general Formula IV used as starting material may be prepared by subjecting a compound of the general Formula XI to cyclisation.

According to process ($c_2$) of the present invention a compound of the general Formula VIII is subjected to ring-closure. The cyclisation may be carried out in the presence of an acidic catalyst, e.g. mineral acids (such as hydrochloric acid, sulfuric acid, polyphosphoric acid etc. or Lewis acids) (e.g. aluminium chloride, boron trifluoride, zinc chloride, tin chloride etc.). One may work particularly advantageously in the presence of sulfuric acid as catalyst.

The reaction is carried out in an inert organic solvent. As reaction medium halogenated hydrocarbons (e.g. methylene chloride, chloroform etc.) can be used. The reaction temperature depends on the activity of the catalyst; the reaction may be generally carried out at 0°–80° C.

The compounds of the general Formula I can be isolated by methods known per se. If sulfuric acid is used as catalyst, one may proceed preferably by pouring the sulfuric acid solution onto ice, making the mixture alkaline and purifying the compound of the general Formula I by extraction with an organic solvent (e.g. chloroform).

The starting materials of the general Formula VIII may be prepared by reacting a compound of the general Formula XI with a chloro halogeno formiate of the general Formula VII. The reaction can be carried out in an analogous manner to process ($c_1$).

The compounds of the general Formula VIII thus obtained may be subjected to cyclisation after or—preferably—without isolation.

The compounds of the general Formula I thus obtained may be converted into their addition salts formed with pharmaceutically acceptable acids. The salt formation can be carried out by generally known and usual methods. Thus one may proceed preferably by reacting a compound of the general Formula I with the corresponding acid in a suitable inert organic solvent. The acid is preferably used in a stoichiometrical amount. One may also proceed by setting free the compound of the general Formula I from a pharmaceutically unacceptable salt with the aid of a strong base and reacting the free base of the general Formula I with the corresponding pharmaceutically acceptable acid.

The new compounds of the general Formula I and pharmaceutically acceptable acid addition salts thereof possess useful pharmaceutical properties and exhibit particularly valuable central nervous system effects. The compounds of the present invention are particularly useful as active ingredient in antidepressants and antiparkinson agents.

According to a further feature of the present invention there are provided pharmaceutical compositions comprising one or more compound(s) of the general Formula I or a pharmaceutically acceptable acid addition salt thereof in admixture with suitable inert pharmaceutical carriers and/or excipients.

The pharmaceutical compositions may be finished in forms suitable for oral (e.g. tablets, capsules, pills, coated pills, dragees, solutions, emulsions, suspensions) or parenteral) (e.g. injections) application. The pharmaceutical compositions may contain usual inert solid or liquid carriers (e.g. talc, starch, magnesium stearate, magnesium carbonate, calcium carbonate, water, alcohols, polyalkylene glycols etc.). The compositions may also comprise usual pharmaceutical auxiliary agents (e.g. wetting agents, disintegrating agents, flavourants, taste-amending additives etc.).

The pharmaceutical compositions according to the present invention can be prepared by methods of pharmaceutical industry known per se.

Further details of the present invention are to be found in the Examples without limiting the scope of the invention to the said Examples.

The pharmacological activity of the compounds of the present invention is determined by the following tests:

1. Acute toxicity; s.c. administration; $LD_{50}$ value measured after a 96 hour observation period.
2. S.c. dose which inhibits the catalepsy induced by a 13 umole/kg dose of Haloperidol, in 50% of the mice.
3. Lowest i.p. dose which still increases or decreases the spontaneous motility of the mice.
4. S.c. dose which inhibits the catalepsy induced by a 110 umole/kg dose of tetrabenazine, in 50% of the mice.
5. S.c. dose which inhibits the ptosis induced by a dose of 79 umole/kg of tetrabenazine, in 50% of the mice.
6. The lowest s.c. dose which still hinders the decrease of the rectal temperature caused by the administration of a 1,6 umole/kg dose of reserpine.
7. The lowest i.v. dose which still increases the blood pressure and nictitating membrane effect on cats.
8. The lowest s.c. dose which still induces stereotypy, in rats.
9. The dose which induces the characteristic circling behaviour after the electrolytic lesion of the substantia nigra.
10. The dose which induces a significant decrease of the prolactine level after 4 days treatment with a dose of 0.073 umole/kg of oeastradiol, on three weeks earlier ovariectomised rats.

The following test compounds are used:

Compound A = product of Example 4
Compound B = product of Example 8
Compound C = product of Example 10
Compound D = product of Example 11
Compound E = product of Example 17
Compound F = product of Example 18
Compound G = product of Example 13
Compound H = product of Example 12
Compound I = product of Example 20
Nomifensine = reference compound, 8-amino-4-phenyl-2-methyl-1,2,3,4-tetrahydro-isoquinoline, described in British Pat. No. 1,164,192.

The test results are summarized in the following Tables I and II.

TABLE I

| Test Compound | 1 ED | 2 TI | ED+/− | 3 TI | 4 ED | TI | 5 ED | TI | 6 ED | TI | $\frac{ED_2}{ED_4}$ |
|---|---|---|---|---|---|---|---|---|---|---|---|
| Nomifensine | 1128 | 56 | 20 | 28+ | 40 | 37 | 30 | 4,2 | 268 | 28 | 40 | 1,6 |
| A | 653 | 86 | 8 | 206− | 3 | 62 | 11 | 43 | 15 | 86 | 8 | 1,4 |
| B | 1925 | 428 | 5 | 342− | 6 | 321 | 6 | 267 | 7 | 428 | 5 | 1,3 |
| C | 686 | 53 | 13 | 42− | 16 | 51 | 13 | 14 | 49 | 11 | 62 | 1,0 |
| D | 637 | 48 | 13 | >40 | <16 | 27 | 24 | 7,8 | 82 | 10 | 64 | 1,8 |
| E | >2049 | 246 | >8 | 31− | >66 | 90 | >23 | 31 | >66 | >205 | | 2,7 |
| F | >2566 | >214 | >12 | 43− | >60 | 128 | >20 | 32 | >80 | 86 | >30 | >1,7 |
| G | 664 | 29 | 23 | 10− | 66 | 71 | 9 | 5 | 133 | 21 | 32 | 0,4 |
| H | 706 | 33 | 21 | 22− | 32 | 99 | 7 | 12 | 59 | 44 | 16 | 0,3 |
| I | 2176 | 55 | 40 | 7.9− | 275 | 13 | 167 | 1,6 | 1360 | 26 | 84 | 4,2 |

TABLE II

| Test Compound | TESTS | | | |
|---|---|---|---|---|
| | 7 | 8 | 9 | 10 |
| Nomifensine | 1,4 | 23 | 42 | 28 |
| A | 5,2 | 89 | 144 | |
| B | 4,3 | >178 | | 96 |
| C | 1,1 | 68 | | |
| D | 1,0 | 64 | | 36 |
| E | 6,1 | 275 | | 143 |
| F | >11 | 178 | | 107 |
| G | 2,1 | 108 | | |
| H | 2,2 | 183 | | |
| I | 1,3 | 21 | 39 | 26 |

The acute toxicity data are determined in mice. Tests 2–6 are also carried out in mice. The doses are expressed in micromole/kg. The therapeutical index (TI) is the LD/ED quotient.

In Test 3 "+ = motility increase" and "− = motility decrease."

The sign ">" means that in the given dose the compound is inactive.

TBZ = Tetrabenazine.

Tests 7–10 are carried out in cats and rats, the doses are expressed in micromole/kg.

Tests 2, 8, 9 and 10 are suitable for the evaluation of the dopaminerg stimulating effect of the test compounds (potential anti-parkinson agent). Tests 4, 5, 6 and 7 give information about the catecholamine-uptake inhibiting effect (potential antidepressive activity).

The reference compound Nomifensine is a well-known anti-parkinsone and antidepressive agent.

The new compounds of the general Formula I do not increase the spontaneous motility of mice, contrary to Nomifensine which increases the spontaneous motility. The absence of the said amphetamine-like psychomotoric stimulating effect is favourable from therapeutical point of view.

Compound C surpasses the activity of Nomifensine in three tests. Compound D is more active than Nomifensine in several tests too and in the anti-reserpine test shows a more favourable therapeutical index. Compounds G and H exhibit very high activity and show good therapeutical index. Compound I possesses outstanding therapeutical properties. Its toxicity is much lower and its activity is higher than that of Nomifensine—the therapeutical index of Compound I is about 2–6,8 times higher in the various tests than that of Nomifensine.

On comparing the dopaminerg type anti-haloperidol test and the anti-tetrabenazine activity being characteristic of the antidepressive effect the following can be stated:

The quotient of the ED values of Columns 2 and 4 is the highest for Compound I (55:13 = 4.2). This means that this compound is relatively a stronger antidepressant than an antiparkinsone agent. The said quotient is high in the case of Nomifensine (1.6), Compound D (1.8), Compound E (2.7) and Compound F (1.7).

On the other hand, the said quotient is low in the case of Compounds G and H which exhibits a stronger anti-dopamine, anti-parkinsone activity.

EXAMPLE 1

8-Ethylamino-acetylamino-4-phenyl-2-methyl-1,2,3,4-tetrahydro-isoquinoline-maleate A mixture of 5.3 g (0.015 mole) of 4-phenyl-8-chloroacetyl-amino-2-methyl-1,2,3,4-tetrahydro-isoquinoline-hydrochloride, 15 ml (10.4 g, 0.23 mole) of ethyl amine and 50 ml of ethanol is reacted in a bomb tube at 60° C. for 5 hours. The reaction mixture is evaporated, the residual oil (7.1 g) is triturated with 50 ml of water, the mixture is made alkaline by adding 30 ml of a 30% aqueous sodium hydroxide solution under stirring and cooling. The mixture is extracted ten times with 100 ml of ether each. The ether solution is dried over anhydrous sodium sulfate and evaporated. The residual oil is rubbed with petrolether. Thus 4.3 g (0.0133 mole) of crude 8-ethylamino-acetylamino-4-phenyl-2-methyl-1,2,3,4-tetrahydro-isoquinoline are obtained in the form of a yellowish-white powder.

The base thus obtained is dissolved in 30 ml of ethanol and a solution of 1.6 g (0.01238 mole) of maleic acid and 15 ml of ethanol is added. The precipitated product is filtered off. Thus 5.2 of the title compound are obtained, mp.: 169° C. On recrystallization from 50 ml of ethanol 4.7 g of the pure title compound are obtained. Yield: 71.2%. Mp.: 170° C.

Analysis: $C_{24}H_{29}N_3O_4$ (439.515): Calculated: C% = 65.60; H% = 6.65; N% = 9.56; Found: C% = 65.38; H% = 6.74; N% = 9.62.

The 8-ethylamino-acetylamino-4-phenyl-2-methyl-1,2,3,4-tetrahydro-isoquinoline base melts at 111° C. from a mixture of benzene and petrolether.

Analysis: $C_{20}H_{25}N_3O$ (323.439): Calculated: C%=74.27; H%=7.79; N%=12.99; Found: C%=74.41; H%=7.97; N%=13.13.

The starting material may be prepared as follows:

31.9 g (0.09 mole) of 8-amino-4-phenyl-2-methyl-1,2,3,4-tetrahydro-isoquinoline-maleate are dissolved in 200 ml of water, whereupon 500 ml of ether are added and the mixture is made alkaline by adding 150 ml of a 30% aqueous sodium hydroxide solution under cooling and stirring. The ether phase is separated and the aqueous layer is further extracted three times with 300 ml of ether each. The united ether solution is dried over anhydrous sodium sulfate and evaporated in vacuo (25° C./20 Torr). The residual yellow oil (22.5 g) is dissolved in 600 ml of anhydrous benzene and a solution of 7.6 ml (11.4 g, 0.101 mole) of chloro acetyl chloride and 40 ml of anhydrous benzene is added dropwise under stirring. The reaction mixture is refluxed for 2 hours and cooled. The precipitated product is filtered, washed three times with 60 ml of anhydrous benzene each and three times with 70 ml of anhydrous ether each. Thus 32 g of a white powder are obtained. Mp.: 217° C. (decomposition). On recrystallization from 230 ml of ethanol 25.5 g of the desired compound are obtained in the form of a white powder. Yield: 81%, mp.: 222° C. (decomposition).

Analysis: $C_{18}H_{20}Cl_2N_2O$, M=351.278: Calculated: C%=61.54; H%=5.74; N%=7.97; Cl%=20.19; Cl$^-$%=10.09. Found: C%=61.23; H%=5.66; N%=8.00; Cl%=20.41; Cl$^-$%=10.17.

The starting material may also be prepared as follows:

3.12 g (0.012 mole) of N-(2-amino-benzyl)-1-phenyl-2-methylamino-1-ethanol are dissolved in 70 ml of anhydrous ether, whereupon 0.95 g (0.012 mole) of anhydrous pyridine are added and thereafter 1.62 g (0.0144 mole) of chloro-acetyl-chloride are added dropwise under vigorous stirring and ice cooling at 3°-6° C. The yellowish-white reaction mixture containing a precipitate is stirred at room temperature for 30 minutes, poured into 100 ml icecold water and extracted three times with 100 ml ether each. The ether solution is dried over anhydrous sodium sulfate for 30 minutes and evaporated in vacuo without heating. The crude N-chloroacetyl compound thus obtained is immediately subjected to cyclisation.

The oily product obtained according to the preceeding paragraph is dissolved in 30 ml of dichloro methane, filtered, and poured into 20 ml of concentrated sulfuric acid. The reaction mixture is stirred at 0°-3° C. for 15 minutes and thereafter stirring is continued for a further 20 minutes. The reaction mixture is poured onto 100 g of ice and extracted four times with 200 ml of chloroform each. The organic phase is dried over anhydrous sodium sulfate and evaporated in vacuo. Thus 3.0 g of an orange powder are obtained. This product is washed three times with 30 ml of ether each. Thus 2.3 g of a beige powder are obtained. On recrystallization from ethanol 1.6 g of 4-phenyl-8-chloro-acetyl-amino-2-methyl-1,2,3,4-tetrahydro-isoquinoline are obtained in the form of a white powder, yield 42.4%. Mp.: 240° C. (decomposition).

Analysis: $C_{18}H_{19}ClN_2O$, M=314.817: Calculated: C%=68.67; H%=6.08; N%=8.90; Cl%=11.26.

Found: C%=68.42; H%=5.95; N%=8.96; Cl%=11.12.

1.5 g (0.00475 mole) of the above base are suspended in 5 ml of ethanol, whereupon 5 ml of ether saturated with hydrogen chloride are added under heating and the solution is made cloudy by adding ether. The precipitated product is filtered in the cold. Thus 1,5 of 4-phenyl-8-chloroacetylamino-2-methyl-1,2,3,4-tetrahydro-isoquinoline-hydrochloride are obtained in the form of a white powder. Yield 38.2%. Mp.: 222° C. (decomposition).

EXAMPLE 2

Preparation of 4-phenyl-2-methyl-8-isopropylamino-acetylamino-1,2,3,4-tetrahydro-isoquinoline-maleate A mixture of 4.27 g (0.0122 mole) of 4-phenyl-8-chloro-acetyl-amino-2-methyl-1,2,3,4-tetrahydro-isoquinoline-hydrochloride, 50 ml of ethanol and 15 ml (10.4 g, 0.176 mole) of isopropyl amine is heated to boiling for 5 hours. The reaction mixture is evaporated and the sticky residue (6.5 g) is dissolved in 100 ml of water and the solution is made alkaline by adding 10 ml of a 30% sodium hydroxide solution under stirring and cooling. The aqueous layer is extracted five times with 200 ml of ether each and the united ether solutions are dried over anhydrous sodium sulfate and evaporated in vacuo. The residual yellow oil (4.4 g) is dissolved in 50 ml of ethanol and a solution of 3.5 g (0.03 mole) of maleic acid and 10 ml of ethanol is added under stirring. The precipitated product is filtered in the cold, washed twice with 10 ml of ethanol each (6 g) and recrystallized from 45 ml of ethanol. Thus 5.3 g of the dimaleinate salt are obtained, mp.: 170° C.

The above dimaleinate salt is dissolved in 30 ml of water and 100 ml of ether are added. The solution is made alkaline by adding 10 ml of a 30% aqueous sodium hydroxide solution under stirring and cooling. The ether phase is separated, the aqueous layer is extracted twice with 100 ml and twice with 50 ml of ether each. The united ether extracts are dried over anhydrous sodium sulfate and the ether is evaporated in vacuo. Thus 3.15 g (9.35 millimole) of the crude base are obtained (mp.: 89° C.). This crude base is dissolved in 47 ml of ethanol and a solution of 1.1 g (9.45 millimole) of maleic acid and 30 ml of ether is added. A white powder (4.1 g) is obtained which is recrystallized from 40 ml of ethanol to give 3.45 g of the title compound. Yield 62.6%, mp.: 134° C.

Analysis: $C_{25}H_{31}N_3O_5$, M=453.543: Calculated: C%=66.22; H%=6.89; N%=9.29. Found: C%=66.23; H%=7.03; N%=9.33.

The free base forms yellowish-white crystals melting at 91° C. from a mixture of benzene and petrolether.

Analysis: $C_{21}H_{27}N_3O$: Calculated: C%=74.74; H%=8.07; N%=12.45. Found: C%=74.68; H%=8.21; N%=12.49.

EXAMPLE 3

Preparation of 8-butylamino-acetylamino-4-phenyl-2-methyl-1,2,3,4-tetrahydro-isoquinolinemaleate A mixture of 3.5 g (0.01 mole) of 4-phenyl-8-chloro-acetylamino-2-methyl-1,2,3,4-tetrahydro-isoquinoline-hydrochloride, 50 ml of ethanol and 10 ml (7.39 g, 0.1 mole) of butyl amine is refluxed for 5 hours. The reaction mixture is evaporated in vacuo and the residue is washed ten times with 50 ml of anhydrous ether each. The ether washing liquid is evaporated to dryness in vacuo, the residue is stirred three times with 10 ml of benzene each, the benzene being evaporated in each case. Thus 3.3 g of a yellowish oil are obtained. This oil is dissolved in 30 ml of ethanol and a solution of 1.2 g (0.01 mole) of maleic acid and 10 ml of ethanol is added. The precipitate (2.9 g, mp.: 172° C.) is recrystallized from ethanol. Thus 2.3 g of the pure title compound are obtained, yield 49.2%, mp.: 174° C.

Analysis: $C_{26}H_{33}N_3O_5$, M=467.57: Calculated: C%=66.79; H%=7.11; N%=8.99. Found: C%=66.80; H%=7.10; N%=9.24.

EXAMPLE 4

Preparation of 4-phenyl-2-methyl-8-pyrrolidino-acetylamino-1,2,3,4-tetrahydro-isoquinoline-dimaleate A mixture of 7.0 g (0.02 mole) of 4-phenyl-8-chloro-acetylamino-2-methyl-1,2,3,4-tetrahydro-isoquinoline-hydrochloride, 70 ml of ethanol and 20 ml (17.0 g, 0.24 mole) of pyrrolidine is refluxed for 5 hours. The reaction mixture is evaporated in vacuo, the residue is dissolved in a mixture of 100 ml of water and 100 ml of ether and the mixture is made alkaline by adding 30 ml of a 30% aqueous sodium hydroxide solution under cooling and stirring. The layers are separated, the aqueous phase is extracted five times with 100 ml of ether each, the organic phase is dried over anhydrous sodium sulfate, clarified with activated charcoal and evaporated. The residue is dissolved in 100 ml of warm ethanol and a solution of 6.6 g (0.057 mole) of maleic acid and 40 ml of ethanol is added. The product is precipitated by adding 1000 ml of ether. The sticky solid dimaleate salt is dissolved in 100 ml of water and the solution is made alkaline by adding 60 ml of a 30% aqueous sodium hydroxide solution under cooling and stirring. The aqueous layer is extracted once with 200 ml and four times with 100 ml of ether each. The ether phases are united, dried over anhydrous sodium sulfate and clarified with activated charcoal. The ether is evaporated and the residue is washed with a mixture of ether and petrolether. Thus 5.4 g of 4-phenyl-2-methyl-8-pyrrolidino-acetylamino-1,2,3,4-tetrahydro-isoquinoline are obtained in the form of white crystals (0.0154 mole). Mp.: 130° C.

The free base thus obtained is suspended in 100 ml of ethanol and a solution of 3.6 g (0.0315 mole) of maleic acid and 36 ml of ethanol is added. After the base is dissolved, the solution is diluted with 150 ml of ether, the precipitate product is filtered in the cold (9 g) and recrystallized from ethanol and ether. Thus 7.3 g of the title compound are obtained, yield 2.9%, mp.: 120° C.

Analysis: $C_{30}H_{35}N_3O_9$, M=581.62: Calculated: C%=61.95; H%=6.07; N%=7.22. Found: C%=61.64; H%=6.40; N%=6.93.

The free base forms white crystals melting at 130° C.
Analysis: $C_{22}H_{27}N_3O$ Calculated: C%=75.61; H%=7.81; N%=12.02. Found: C%=75.77; H%=8.02; N%=12.16.

EXAMPLE 5

Preparation of 4-phenyl-2-methyl-8-piperidino-acetylamino-1,2,3,4-tetrahydro-isoquinoline-dimaleate A mixture of 4.3 g (0,0122 mole) of 4-phenyl-8-chloro-acetylamino-2-methyl-1,2,3,4-tetrahydro-isoquinoline-hydrochloride, 70 ml of ethanol and 15 ml (12.9 g, 0.15 mole) of piperidine is refluxed for 5 hours. The reaction mixture is evaporated, the residue is dissolved in 100 ml of water and made alkaline by adding 15 ml of a 30% aqueous sodium hydroxide solution under cooling and stirring. The aqueous solution is extracted once with 200 ml and four times with 100 ml of benzene each, the benzene extracts are united, dried over anhydrous sodium sulfate and evaporated. The oily residue (5.6 g) is dissolved in 50 ml of ethanol and a solution of 3.5 g 0.08 mole of maleic acid and 10 ml of ethanol is added. The precipitate is filtered off (5.9 g) and recrystallized from ethanol. Thus 5.0 g of the dimaleate salt are obtained.

The dimaleate salt is dissolved in 30 ml of water and 100 ml of ether are added whereupon the solution is made alkaline by adding 10 ml of a 30% aqueous sodium hydroxide solution under stirring and cooling. The layers are separated, the aqueous phase is extracted once with 100 ml and twice with 50 ml of ether each, the united ether solutions are dried over anhydrous sodium sulfate and evaporated. Thus 3.2 g (0.0085 mole) of 4-phenyl-2-methyl-8-piperidino-acetyl-amino-1,2,3,4-tetrahydro-isoquinoline are obtained in the form of a yellowish-white product.

The free base thus obtained is dissolved in 38 ml of ethanol and 2.03 g (0.0175 mole) of maleic acid are added. The solution is diluted with 20 ml of ether. The precipitated product is filtered in the cold. The white powder (4.1 g) is recrystallited from ethanol. Thus 3.55 g of the title compound are obtained, yield 61%. The product has a non-characteristic protracted melting point.

Analysis: $C_{31}H_{37}N_3O_9$, M=609.66: Calculated: C%=62.51; H%=6.26; N%=7.05. Found: C%=62.28; H%=6.29; N%=7.20.

The analytical data of the oily base are as follows:
Analysis: $C_{23}H_{29}N_3O$: Calculated: C%=75.99; H%=8.04; N%=11.56. Found: C%=75.60; H%=8.08; N%=11.67.

EXAMPLE 6

Preparation of 4-phenyl-2-methyl-8-morpholino-acetylamino-1,2,3,4-tetrahydro-isoquinoline-dimaleate A mixture of 7 g (0.02 mole) of 4-phenyl-8-chloro-acetylamino-2-methyl-1,2,3,4-tetrahydro-isoquinoline-hydrochloride, 70 ml of ethanol and 20 ml (20.0 g, 0.23 mole) of morpholine is refluxed for 5 hours. The reaction mixture is evaporated in vacuo, the residue is dissolved in a mixture of 200 ml of water and 200 ml of ether, 30 ml of a 30% aqueous sodium hydroxide solution is added, the layers are separated and the aqueous phase is extracted four times with 200 ml of ether each. The united ether solutions are dried over anhydrous sodium sulfate and evaporated. The oily residue (6.7 g) is dissolved in 100 ml of ethanol and a solution of 6.6 g (0.057 mole) of maleic acid and 30 ml of methanol is added. The precipitated product is filtered in the cold. The beige coloured dimaleate (10.7 g) is dissolved in 100 ml of water, the solution is made alkaline by adding 60 ml of a 35% aqueous sodium hydroxide solution and extracted once with 200 ml and four times with 100 ml of ether each. The ether phases are united, dried over anhydrous sodium sulfate, clarified with activated charcoal and dried. The ether is evaporated and the residue is crystallized from a mixture of ether and petrolether.

Thus 5.1 g of (0.014 mole) of white crystalline 4-phenyl-2-methyl-8-morpholino-acetylamino-1,2,3,4-tetrahydro-isoquinoline are obtained. Mp.: 120° C.

The above free base is dissolved in 70 ml of ethanol and a solution of 3.3 g (0.0284 mole) of maleic acid and 30 ml of ethanol is added. The solution is diluted with 15 ml of ether. The precipitated crystals are filtered in the cold. 8.0 g of a white powder are obtained. On recrystallization from ethanol 6.9 g of the title compound are obtained, in the form of white crystals. Yield 58%. Mp.: 176° C. (decomposition).

Analysis: $C_{30}H_{35}N_3O_{10}$, M=597.62: Calculated: C%=60.29; H%=5.90; N%=7.03. Found: C%=60.11; H%=5.83; N%=7.02.

The base forms white crystals melting at 120° C. (ether-petrolether)

Analysis: $C_{22}H_{27}N_3O_2$: Calculated: C%=72.30; H%=7.45; N%=11.50. Found: C%=72.45; H%=7.49; N%=11.58.

EXAMPLE 7

Preparation on
8-[β'-ethylamino-propionylamino]-4-phenyl-2-methyl-1,2,3,4-tetrahydroisoquinoline-maleate A mixture of 4.8 g (0.013 mole) of 4-phenyl-8-3'-chloro-propionyl-amino-2-methyl-1,2,3,4-tetrahydro-isoquinoline-hydrochloride, 50 ml of ethanol and 15 ml (10.4 g, 0.23 mole) of ethyl amine is heated in a bomb tube at 60° C. for 5 hours. The reaction mixture is evaporated, the residual yellow oil is rubbed with 50 ml of water, the solution is made alkaline by adding 20 ml of a 30% aqueous sodium hydroxide solution and extracted five times with 100 ml and three times with 200 ml of benzene each. The organic layers are united, dried over anhydrous sodium sulfate and evaporated in vacuo. Thus 3.5 g of a yellowish-white powder are obtained (0.0104 mole of the crude base).

The crude base thus obtained is dissolved in 35 ml of ethanol and a solution of 1.2 g (0.010 mole) of maleic acid and 5 ml of methanol is added. The solution is diluted with 100 ml of ether and cooled. The precipitated product is filtered off. This product (4.0 g) is recrystallized from ethanol. Thus 2.8 g of the title compound are obtained, yield 47.4%. The white crystals melt at 162° C.

Analysis: $C_{25}H_{31}N_3O_5$, M=453.54: Calculated: C%=66.22; N%=6.89; N%=9.29. Found: C%=66.13; N%=7.07; N%=9.47.

The starting material may be prepared as follows:

39 g (0.11 mole) of 8-amino-4-phenyl-2-methyl-1,2,3,4-tetrahydro-isoquinoline-maleate are dissolved in 200 ml of water and 500 ml of ether are added. The solution is made alkaline by adding 150 ml of a 30% aqueous sodium hydroxide solution under cooling and stirring. The ether layer is separated and the aqueous phase is extracted three times with 300 ml of ether each. The united ether solutions are dried over anhydrous sodium sulfate and evaporated in vacuo. The residual yellow oil (24.3 g) is dissolved in 600 ml of anhydrous benzene and a solution of 14.2 g (0.112 mole) of 3-chloro-propionic acid and 50 ml benzene is added within 20 minutes and the reaction mixture is boiled for 2 hours. The mixture is cooled, the precipitated product filtered, washed with ether and dried on the air. Thus 32.0 g of a white powder are obtained. This product is recrystallized from ethanol on diluting with 50 ml of warm ether. Thus 22.5 g of the desired compound are obtained, yield 60.4%. The white crystals melt at 220° C. (decomposition).

Analysis: $C_{19}H_{22}N_2OCl_2$, M=365.305: Calculated: C%=62.47; H%=6.07; N%=7.67; Cl%=19,63; Cl$^-$%=9,81. Found: C%=62.72; H%=6.17; N%=7.68; Cl%=19.33; Cl$^-$%=9.60.

EXAMPLE 8

Preparation of
4-phenyl-8-[3'-isopropylamino-propionyl-amino]-2-methyl-1,2,3,4-tetrahydroisoquinoline-maleate A mixture of 4.8 g (0.013 mole) of 4-phenyl-8-3'-chloro-propionyl-amino-2-methyl-1,2,3,4-tetrahydro-isoquinoline-hydrochloride, 50 ml of ethanol and 15 ml (10.4 g, 0.176 mole) of isoprcpyl amine is refluxed for 5 hours whereupon the reaction mixture is evaporated in vacuo. The residue is dissolved in 50 ml of water, made alkaline by adding 20 ml of a 30% aqueous sodium hydroxide solution under cooling and stirring and extracted six times with 150 ml of benzene each. The benzene solution is dried over anhydrous sodium sulfate and evaporated in vacuo. The residual white oil (5.3 g) is dissolved in 50 ml of ethanol and 1.5 g (0.013 mole) of maleic acid are added. The solution is diluted with 50 ml of ether, cooled, the precipitated product is filtered off. The white powder (5.6 g) is recrystallized from ethanol. Thus 5.0 g of the title compound are obtained, yield 77.2%. The white crystals melt at 158° C.

Analysis: $C_{26}H_{33}N_3O_5$, M=467.57: Calculated: C%=66.79; H%=7.11; N%=8.99. Found: C%=66.77; H%=7.32; N%=8.93.

EXAMPLE 9

Preparation of
8-[3'-butyl-amino-propionylamino]-4-phenyl-2-methyl-1,2,3,4-tetrahydroisoquinoline-maleate A mixture of 4.8 g (0.013 mole) of 4-phenyl-8-3'-chloro-propionyl-amino-2-methyl-1,2,3,4-tetrahydroisoquinoline-hydrochloride, 50 ml of ethanol and 15 ml (11.0 g, 0.15 mole) of butyl amine is refluxed for 5 hours. The reaction mixture is evaporated in vacuo, the residue is suspended in 50 ml of water, made alkaline by adding 20 ml of a 30% by weight aqueous sodium hydroxide solution and extracted six times with 150 ml of ether each. The ether solutions are united, dried over anhydrous sodium sulfate and evaporated in vacuo. The residual colourless oil (5.3 g) is dissolved in 60 ml of ethanol and reacted with 1.3 g (0.0112 mole) of maleic acid. The solution is diluted with 100 ml of ether and cooled. The precipitated product is filtered (5.6 g) and recrystallized from ethanol. Thus 4.5 g of the title compound are obtained. Yield 71.8%. The white crystals melt at 147° C.

Analysis: $C_{27}H_{35}N_3O_5$, M=481.60: Calculated: C%=67.34; H%=7.33; N%=8.72. Found: C%=67.49; H%=7.60; N%=8.67.

EXAMPLE 10

Preparation of
8-ethylamino-acetyl-amino-4-p-chloro-phenyl-2-methyl-1,2,3,4-tetrahydroisoquinoline-maleate A mixture of 7.6 g of 8-chloro-acetyl-amino-4-p-chloro-phenyl-2-methyl-1,2,3,4-tetrahydro-isoquinoline-hydrochloride, 100 ml of ethanol and 40 ml (27.8 g, 0.61 mole) (of ethyl amine is heated in a bomb tube at 60° C. for 5 hours. The reaction mixture is evaporated, the residual yellow oil is suspended in 50 ml of water and made alkaline by adding 30 ml of a 35% aqueous sodium hydroxide solution and extracted with ether. The ether solution is dried over anhydrous sodium sulfate and evaporated. Thus 8.1 g of a yellow oil are obtained which is dissolved in 30 ml of ethanol and reacted with a solution of 2.3 g (0.02 mole) of maleic acid in 5 ml of ethanol. The solution is diluted with 40 ml of ether. The precipitated product is filtered off and dried (10 g) and recrystallized from ethanol. Thus 6.2 g of the title compound are obtained, yield 65.2%. The white microcrystals melt at 189° C. (decomposition).

Analysis: $C_{24}H_{28}ClN_3O_5$, M=473.96: Calculated: C%=60.82; H%=5.95; Cl%=7.48. Found: C%=60.98; H%=6.04; Cl%=7.56.

The starting material can be prepared as follows:

To a solution of 10.9 g (0.04 mole) of crude 8-amino-4-p-chloro-phenyl-2-methyl-1,2,3,4-tetrahydro-isoquinoline and 220 ml of anhydrous benzene a solution of 5.4 g (0.047 mole, 3.6 ml) of chloro-acetyl chloride and 30 ml of anhydrous benzene is added under stirring. The addition having been completed the reaction mixture is heated to boiling for 2.5 hours. The mixture is cooled and the precipitated product is filtered off, washed with benzene, acetone and ether and dried. Thus 14 g of 8-chloro-acetyl-amino-4-p-chloro-phenyl-2-methyl-1,2,3,4-tetrahydro-isoquinoline-hydrochloride are obtained. Yield 90.9%. The white powder melts at 220° C. (decomposition).

Analysis: $C_{18}H_{19}Cl_3N_2O$, M=384.7: Calculated: C%=56.05; H%=4.96; N%=7.26; Cl%=27.25; Cl⁻%=9,08. Found: C%=56.21; H%=5.12; N%=7.42; Cl%=27.32; Cl⁻%=9.12.

EXAMPLE 11

Preparation of 8-butyl-amino-acetyl-amino-4-p-chloro-phenyl-2-methyl-1,2,3,4-tetrahydro-isoquinoline-maleate A mixture of 6.2 g (0.016 mole) of 8-chloro-acetyl-amino-4-p-chloro-phenyl-2-methyl-1,2,3,4-tetrahydro-isoauinoline-hydrochloride, 120 ml of ethanol and 20 ml (14.78 g, 0.2 mole) of butyl amine is refluxed for 5 hours. The reaction mixture is evaporated in vacuo and the residue is taken up in 50 ml of water and made alkaline with 25 ml of a 30% aqueous sodium hydroxide solution under cooling and stirring. The mixture is extracted six times with 150 ml of benzene each, the benzene solutions are united, dried over anhydrous sodium sulfate and the solvent is distilled off. The yellow residue (7.3 g) is dissolved in 200 ml of ethanol and a solution of 1.9 g (0.064 mole) of maleic acid and 5 ml of ethanol is added. The solution is diluted with 400 ml of ether, the precipitated product is filtered off (7 g, mp.: 152° C.) and recrystallized from ethanol. Thus 4.6 g of the title compound are obtained, yield 57.5%. The white microcrystals melt at 154° C.

Analysis: $C_{26}H_{32}ClN_3O_5$, M=502.018: Calculated: C%=62.21; H%=6.43; N%=8.37; Cl%=7.06. Found: C%=62.36; H%=6.70; N%=8.38; Cl%=7.04.

EXAMPLE 12

Preparation of 8-ethylamino-acetyl-amino-2-methyl-4-p-tolyl-1,2,3,4-tetrahydro-isoquinoline maleate A mixture of 5.2 g (0.0145 mole) of 8-chloro-acetyl-amino-2-methyl-4-p-tolyl-1,2,3,4-tetrahydro-isoquinoline-hydrochloride, 100 ml of ethanol and 30 ml (20.8 g, 0.45 mole) of ethyl amine is heated in a bomb tube at 70° C. for 5 hours. The reaction mixture is evaporated, the residual orange oil is dissolved in 50 ml of ethanol and reacted with 1.8 g (0.0155 mole) of maleic acid. The solution is diluted with 150 ml of ether in portions, cooled, and the precipitated product is filtered off and washed with a mixture of acetone and ether. The product 5.7 g, [white powder, mp.: 157° C. (decomposition)] is recrystallized from a mixture of ethanol and ether. Thus 4.3 g of the title compound are obtained. Yield 66%, mp.: 176° C. (decomposition).

Analysis: $C_{25}H_{31}N_3O_5$, M=453.546: Calculated: C%=66.20; H%=6.89; N%=9.26. Found: C%=66.10; H%=7.39; N%=9.25.

The starting material can be prepared as follows:

To a solution of 7.6 g (0.03 mole) of 8-amino-2-methyl-4-p-tolyl-1,2,3,4-tetrahydro-isoquinoline and 100 ml of anhydrous benzene a solution of 4.05 g (0.035 mole, 2.7 ml) of chloro-acetyl chloride and 30 ml of anhydrous benzene is added dropwise under stirring. The reaction mixture is heated to boiling for 5 hours and cooled. The precipitated product is filtered off, washed with ether and dried. Thus 10.1 g of 8-chloro-acetyl-amino-2-methyl-4-p-tolyl-1,2,3,4-tetrahydro-isoquinoline-hydrochloride are obtained, yield 92.6%. The white powder melts at 228° C. (decomposition).

Analysis: $C_{19}H_{22}Cl_2N_2O$, M=365.3: Calculated: C%=62.47, H%=6.07, N%=7.67, Cl%=19.41, Cl⁻%=9.70. Found: C%=62.69, H%=6.45, N%=7.58, Cl%=19.64, Cl⁻%=9.73.

EXAMPLE 13

Preparation of 8-butylamino-acetyl-amino-2-methyl-4-p-tolyl-1,2,3,4-tetrahydro-isoquinoline-maleate A mixture of 4.9 g (0.0135 mole) of 8-chloro-acetyl-amino-2-methyl-4-p-tolyl-1,2,3,4-tetrahydro-isoquinoline-hydrochloride, 300 ml of ethanol and 20 ml (14.78 g, 0.12 mole) of butyl amine is heated to boiling for 5 hours. The reaction mixture is evaporated to dryness, the residue is taken up in 50 ml water and made alkaline by adding 25 ml of a 30% aqueous sodium hydroxide solution under cooling and stirring. The mixture is extracted five times with 150 ml of ether each, the organic layers are united, dried and the solvent is distilled off in vacuo. The residual yellowish-white oil is taken up in 50 ml of ethanol and reacted with a solution of 1.6 g (0.0148 mole) of maleic acid. To the mixture 50 ml of ether are added. After cooling the precipitated product is filtered off and washed with a mixture of acetone and ether and dried. Thus 6 g of the title compound are obtained, yield 92.0%. The white powder melts at 172° C. (decomposition).

Analysis: $C_{27}H_{35}N_3O_5$, M=481.6: Calculated: C%=67.34; H%=7.33; N%=8.73. Found: C%=67.60; H%=7.50; N%=8.47.

EXAMPLE 14

Preparation of 8-ethyl-carbamoyl-amino-4-phenyl-2-methyl-1,2,3,4-tetrahydro-isoquinoline-maleate A mixture of 3.6 g (0.015 mole) of 8-amino-4-phenyl-2-methyl-1,2,3,4-tetrahydro-isoquinoline, 1.17 g (0.0165 mole) of ethyl isocyanate and 40 ml of anhydrous benzene is refluxed for 2 hours. The reaction mixture is evaporated in vacuo, the residue is dissolved in 40 ml of chloroform, the solution is subjected to chromatography on a silicagel column and eluted subsequently with 250 ml of chloroform containing 10% of ethanol and 250 ml of chloroform containing 20% of ethanol. The united eluates are evaporated, the residue (3.8 g) is treated with petrolether. The solid product is reacted with a solution of 3.5 g (0.029 mole) of maleic acid in 60 ml of ethanol. The reaction mixture is diluted with 200 ml of ether and cooled. The precipitated product is filtered off (5.0 g) and recrystallized from a mixture of ethanol and ether. Thus 4.5 g of the title compound are obtained. Mp.: 137°–139° C. (decomposition). On recrystallization from ethanol 3.7 g of the purified title compound are obtained. Yield 77%, mp.: 140° C. (decomposition).

Analysis: $C_{23}H_{27}N_3O_5$, 425.49: Calculated: C%=64.93; H%=6.40; N%=9.88. Found: C%=65.13; H%=6.49; N%=9.92.

EXAMPLE 15

Preparation of 4-phenyl-2-methyl-8-n-propyl-carbamoyl-amino-1,2,3,4-tetrahydro-isoquinoline-maleate One proceeds according to Example 14 except that n-propyl isocyanate is used in the place of ethyl isocyanate. Thus 3.5 g of the title compound are obtained in the form of yellowish-white crystals. Yield 53.0%, mp.: 149°–150° C.

Analysis: $C_{24}H_{29}N_3O_5$, 439.515: Calculated: C%=65.59; H%=6.65; N%=9.56. Found: C%=65.80; H%=7.08; N%=9.48.

EXAMPLE 16

Preparation of 8-n-butyl-carbamoyl-amino-4-phenyl-2-methyl-1,2,2,3,4-tetrahydro-isoquinoline-maleate One proceeds according to Example 14 except that n-butyl isocyanate is used in the place of ethyl isocyanate. Thus 1.9 g of the title compound are obtained in the form of a white powder. Yield: 42%. M.p.: 145° C. (decomposition).

Analysis: $C_{25}H_{31}N_3O_5$, 453.54: Calculated: C%=66.20; H%=6.89; N%=9.26. Found: C%=66.32; H%=6.37; N%=9.44.

EXAMPLE 17

Preparation of 8-n-butyl-carbamoyl-amino-4-p-chloro-phenyl-2-methyl-1,2,3,4-tetrahydro-isoquinoline-maleate One proceeds according to Example 14 except that 8-amino-4-p-chloro-phenyl-2-methyl-1,2,3,4-tetrahydro-isoquinoline and n-butyl isocyanate are used as starting material. Thus 7.8 g of the title compound are obtained in the form of a yellowish-white powder, yield 32%, mp.: 134° C. (decomposition).

Analysis: $C_{25}H_{30}ClN_3O_5$, 487.99: Calculated: C%=61.53; H%=6.20; N%=8.61; Cl%=7.27. Found: C%=60.97; H%=6.30; N%=8.64; Cl%=7.51.

EXAMPLE 18

Preparation of 2-methyl-8-n-butyl-carbamoyl-amino-4-p-tolyl-1,2,3,4-tetrahydro-isoquinoline-maleate One proceeds as described in Example 14 except that 8-amino-2-methyl-4-p-tolyl-1,2,3,4-tetrahydro-isoquinoline and n-butyl-isocyanate are used as starting material. Thus 8.4 g of the title compound are obtained in the form a yellowish-white powder. Mp.: 169° C. (decomposition). Yield: 41.5%.

Analysis: $C_{25}H_{30}ClN_3O_5$, 487.99: Calculated: C%=66.79; H%=7.11; N%=8.99. Found: C%=66.30; H%=7.30; N%=8.89.

EXAMPLE 19

Preparation of 8-n-butyl-carbamoyl-amino-4-phenyl-2-methyl-1,2,3,4-tetrahydro-isoquinoline-maleate A mixture of 5.2 g (0.02 mole) of N-2-amino-benzyl-1-phenyl-2-methyl-amino-1-ethanol, 2.2 g (0.022 mole) of n-butyl-isocyanate and 100 ml of anhydrous benzene is refluxed for 2 hours, whereupon the reaction mixture is evaporated in vacuo. 7.2 g of an oil are obtained which solidifies on standing and consists of N-[2-butyl-carbamoyl-amino-benzyl]-1-phenyl-2-methyl-amino-1-ethanol.

7.2 g of the crude product prepared according to the preceding paragraph are dissolved in 100 ml of methylene chloride, the solution is added dropwise to 4.4 ml of concentrated sulfuric acid at 2°–6° C. within 45 minutes and the reaction mixture is stirred at 6° C. for half an hour, poured into 100 g of ice, made alkaline with a 30% aqueous sodium hydroxide solution and extracted four times with 100 ml of chloroform each. The united chloroform extracts are dried over anhydrous sodium sulfate and evaporated in vacuo. Thus 5.4 g of a yellowish-white solid are obtained. The product is dissolved in 30 ml of ethanol and 2.75 g (0.0235 mole) of maleic acid are added. The reaction mixture is diluted with 300 ml of ether in portions, cooled and the precipitated product is filtered off and recrystallized from a mixture of ethanol and ether. Thus 6.0 g of the title compound are obtained, yield 61.6%. Mp.: 145° C. The white powder obtained is identical with the product prepared according to Example 16.

EXAMPLE 20

Preparation of 8-ethoxycarbonylamino-4-p-chloro-phenyl-2-methyl-1,2,3,4-tetrahydroisoquinoline A solution of 13.1 g (0.047 mole) of 8-amino-4-p-chloro-phenyl-2-methyl-1,2,3,4-tetrahydro-isoquinoline and 300 ml of anhydrous benzene is admixed with a solution of 6.8 g (0.0625 mole, 6 ml) of ethyl chloroformate and 60 ml of anhydrous benzene. The reaction mixture is refluxed for 2.5 hours and the benzene is distilled off in vacuo. The residue is dissolved in 10 ml of water, made alkaline with 10 ml of a concentrated ammonium hydroxide solution and extracted three times with 100 ml of chloroform each. The chloroform extracts are united, dried over anhydrous sodium sulfate, evaporated and the residue is recrystallized twice from ethanol. Thus 7.3 g of the title compound are obtained in the form of white crystals, yield 45.6%, Mp.: 155° C.

Analysis: $C_{19}H_{21}ClN_2O_2$, 344.845: Calculated: C%=66.19; H%=6.14; N%=8.12; Cl%=10.28. Found: C%=66.79; H%=5.89; N%=8.42; Cl%=10.56.

EXAMPLE 21

Preparation of
8-ethoxycarbonyl-amino-4-p-chloro-phenyl-2-methyl-1,2,3,4-tetrahydroisoquinoline-hydrochloride 7.3 g of (0.0212 moles) of the base prepared according to Example 20 are suspended in 50 ml of ethanol and 10 ml of ethanol saturated with hydrogen chloride are added under cooling. The mixture is made cloudy by adding 200 ml of ether and the precipitation of the product is made complete by scratching the wall of the flask. The precipitated product is filtered and washed with ether. Thus 8.1 of the title compound are obtained in the form of a white powder. Yield: almost 100%. Mp.: 145°–150° C. decomposition.

Analysis: $C_{19}H_{22}Cl_2N_2O_2$, 381.30: Calculated: C% = 59.85; H% = 5.82; N% = 7.35; Cl% = 18.60; Cl$^-$% = 9.30. Found: C% = 59.74; H% = 6.06; N% = 7.17; Cl% = 18.54; Cl$^-$% = 9.21.

EXAMPLE 22

Preparation of
8-ethoxycarbonylamino-4-phenyl-2-methyl-1,2,3,4-tetrahydro-isoquinoline To a solution of 5.5 g 0.023 mole of 8-amino-4-phenyl-2-methyl-1,2,3,4-tetrahydro-isoquinoline and 50 ml of anhydrous benzene a solution of 3.4 g (0.031 mole) of ethyl chloroformate and 30 ml of anhydrous benzene is added. The reaction mixture is heated to boiling for 3 hours, the benzene is distilled off in vacuo. The residue is dissolved in 5 ml of water, made alkaline with a 30% aqueous sodium hydroxide solution and extracted three times with 50 ml of chloroform each. The chloroform extracts are united, dried over sodium sulfate and evaporated. The residue is washed with some cold ethanol and recrystallized from ethanol. Thus 3.0 g of the title compound are obtained in the form of white crystals. Yield 37.5%. Mp.: 178° C.

Analysis: $C_{19}H_{22}N_2O_2$, 346.86. Calculated: C% = 73.84; H% = 7.15; N% = 9.02. Found: C% = 73.96; H% = 7.51; N% = 8.95.

EXAMPLE 23

Preparation of
8-ethoxycarbonylamino-4-phenyl-2-methyl-1,2,3,4-tetrahydro-isoquinoline 2.6 g (0.01 mole) of N-2-amino-benzyl-1-phenyl-2-methyl-amino-1-ethanol are dissolved in 30 ml of ether. To the solution 0.79 g (0.01 mole) of anhydrous pyridine are added, whereupon 1.3 g (0.012 mole) of ethyl chloroformate are added under vigorous stirring and cooling and the reaction is carried out at 15° C. The reaction mixture which contains a white precipitate is stirred at room temperature for 330 minutes, poured into 30 ml of icecold water, the aqueous phase is extracted three times with 100 ml of ether each, the united ether extracts are dried over anhydrous sodium sulfate and evaporated in vacuo. Thus 2.8 g of N-[2-ethoxycarbonylamino-benzyl]-1-phenyl-2-methyl-amino-1-ethanol are obtained in the form of a yellowish-white oil which can be subjected to further reaction without purification.

2.8 g of the oily residue obtained according to the previous paragraph are dissolved in 40 ml of dichloro methane and the solution is poured into 15.4 ml of concentrated sulfuric acid at 5°–6° C. within half an hour under cooling and stirring. The reaction mixture is stirred at this temperature for a further 20 minutes, and poured onto 60 g of ice. The mixture is made alkaline with a 30% aqueous sodium hydroxid solution under cooling and stirring and extracted six times with 80 ml of chloroform each. The organic phases are united, dried over anhydrous sodium sulfate and evaporated in vacuo. Thus 2.3 g of a yellowish-white solid are obtained. After recrystallization from ethanol 2.0 g of the title compound are obtained in the form of white crystals. Mp: 174° C. Yield 64.5%.

EXAMPLE 24

Preparation of
8-butoxycarbonyl-amino-4-phenyl-2-methyl-1,2,3,4-tetrahydro-isoquinoline A solution of 2.4 g (0.01 mole) of 8-amino-4-phenyl-2-methyl-1,2,3,4-tetrahydro-isoquinoline and 100 ml of anhydrous benzene is admixed with a solution of 1.4 g (0.012 mole) of butyl chloroformate and 10 ml of anhydrous benzene and the reaction mixture is heated to boiling for 2 hours. After cooling the mixture is diluted with 50 ml of icecold water, the pH is adjusted to 9 by adding a concentrated ammonium hydroxide solution, the benzene phase is separated and extracted twice with 20 ml of benzene each, dried over anhydrous sodium sulfate and evaporated in vacuo. Thus 3.6 g of an orange oil are obtained. The product is recrystallized twice from ethanol to give 1.8 g of the title compound, yield 52.9%. Mp: 106° C. (white powder)

Analysis: $C_{21}H_{26}N_2O_2$, M = 338.454: Calculated: C% = 75.43; H% = 6.63; N% = 8.37. Found: C% = 75.19; H% = 6.44; N% = 8.57.

EXAMPLE 25

Preparation of
8-β-chloroethoxycarbonyl-amino-4-phenyl-2-methyl-1,2,3,4-tetrahydro-isoquinoline 3.5 g (0.015 mole) of 8-amino-2-methyl-4-phenyl-1,2,3,4-tetrahydro-isoquinoline are dissolved in 100 ml of anhydrous benzene, 1.28 g (0.016 mole) of anhydrous pyridine are added and a solution of 2.14 g (0.015 mole) of β-chloro-ethyl-chloro-formiate and 10 ml of anhydrous benzene is added dropwise under stirring and cooling at room temperature. The reaction mixture is stirred at room temperature for an hour, poured into 50 ml of ice-cold water, the organic phase is separated and the aqueous layer is extracted three times with 30 ml of benzene each. The united organic solutions are dried over anhydrous sodium sulfate and evaporated to dryness in vacuo. Thus 4.5 g of a yellowish-white substance are obtained. The product is recsystallized twice from ethanol to give 2.7 g of the title compound. Yield 52%. The white crystals melt at 154° C.

Analysis: $C_{19}H_{21}ClN_2O_2$, M = 344.845: Calculated: C% = 66.18; H% = 6.14; N% = 8.12; Cl% = 10.28. Found: C% = 66.29; H% = 6.24; N% = 8.10; Cl% = 10.38.

EXAMPLE 26

Preparation of
8-benzyloxycarbonyl-amino-4-phenyl-2-methyl-1,2,3,4-tetrahydro-isoquinoline 4.6 g (0,02 mole) of 8-amino-4-phenyl-2-methyl-1,2,3,4-tetrahydro-isoquinoline are dissolved in 100 ml of anhydrous benzene. To the solution 6.2 g of 90% benzyloxycarbonyl chloride (5.2 ml, 0.03 mole) are added. The reaction mixture is decomposed with 150 ml of water and made alkaline by adding a 30% aqueous sodium hydroxide solution under ice cooling. The benzene phase is separated and the aqueous layer extracted twice with 150 ml of benzene each and evaporated. The residue is stirred with 150 ml of ether, cooled, the precipitated product is filtered and washed with cold ether. Thus 4.7 g of a yellowish-white powder are obtained. Mp.: 142°-146° C. On recystallization from ethanol 3.6 g of the title compound are obtained, yield 49%. The white crystals melt at 147°-148° C.

Analysis: $C_{24}H_{24}N_2O_2$, M=372.474: Calculated: C%=77.39; H%=6.49; N%=7.50. Found: C%=77.50; H%=6.78; N%=7.70.

2.4 g (0.0064 mole) of the above base are suspended in 70 ml of ether and a solution of 0.75 g (0.0064 mole) of maleic acid and 5 ml of ethanol is added under stirring. The reaction mixture is stirred for 10 minutes and cooled to 0° C. The precipitated product is filtered, washed with a mixture of ethanol and ether and then with ether and recrystallized from ethanol. Thus 2.4 g of 8-benzyloxycarbonyl-amino-4-phenyl-2-methyl-1,2,3,4-tetrahydro-isoquinoline-maleate are obtained. Yield 79%. The white powder melts at 166°-167° C.

Analysis: $C_{28}H_{28}N_2O_6$, M=488.544: Calculated: C%=68.84; H%=5.98; N%=5.73. Found: C%=68.76; H%=5.95; N%=5.82.

What we claim is:

1. 4-aryl-2-methyl-1,2,3,4-tetrahydro-isoquinoline derivatives of the formula I

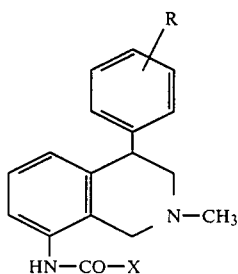

wherein
R stands for hydrogen, lower alkyl or halogen and
X represents a group of the formula $-(CH_2)_n-NR^1R^2$, $-NH-R^3$ or $-OR^4$, in which
$R^1$ and $R^2$ may be the same or different and stand for for hydrogen or lower alkyl or $R^1$ and $R^2$ together with the adjacent nitrogen atom to which they are attached, form a 5- or 6-membered saturated pyrrolidino, piperidino, morpholino, thiomorpholino, piperazino, N-alkylpiperazino or N-benzyl piperazino ring;
n is the integer 1, 2, 3 or 4;
$R^3$ stands for lower alkyl, phenyl or phenyl substituted by halogen or lower alkyl and
$R^4$ is lower alkyl, halogeno lower alkyl, or phenyl lower alkyl
and pharmaceutically acceptable acid addition salts thereof.

2. Compounds according to claim 1 having the formula IA

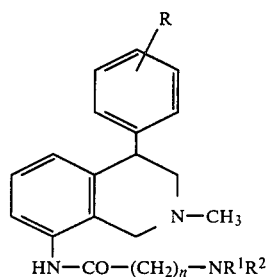

and pharmaceutically acceptable acid addition salts thereof, wherein R, $R^1$, $R^2$ and n have the meanings stated in claim 1.

3. Compounds according to claim 1 having the formula IB

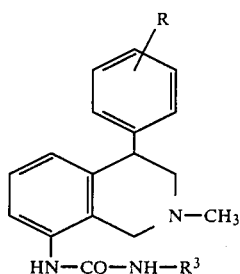

and pharmaceutically acceptable acid addition salts thereof, wherein R and $R^3$ have the meanings stated in claim 1.

4. Compounds according to claim 1 having the formula IC

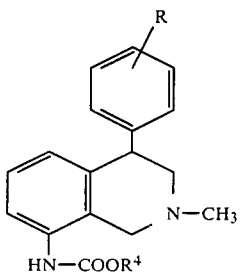

and pharmaceutically acceptable acid addition salts thereof, wherein R and $R^4$ have the meanings stated in claim 1.

5. The compounds of claim 1 which are:
8-Ethylamino-acetylamino-4-p-chlorophenyl-2-methyl-1,2,3,4-tetrahydro-isoquinoline and pharmaceutically acceptable acid addition salts thereof;
8-n-butylamino-acetylamino-4-p-chloro-phenyl-2-methyl-1,2,3,4-tetrahydro-isoquinoline and pharmaceutically acceptable acid addition salts thereof;
8-ethylamino-acetylamino-4-p-tolyl-2-methyl-1,2,3,4-tetrahydro-isoquinoline and pharmaceutically acceptable acid addition salts thereof;
8-n-butylamino-acetylamino-4-p-tolyl-2-methyl-1,2,3,4-tetrahydro-isoquinoline and pharmaceutically acceptable acid addition salts thereof.

6. The compounds of claim 1 which are:

8-n-butyl-carbamoylamino-4-p-chloro-phenyl-2-methyl-1,2,3,4-tetrahydro-isoquinoline and pharmaceutically acceptable acid addition salts thereof;

8-n-butyl-carbamoylamino-4-p-tolyl-2-methyl-1,2,3,4-tetrahydro-isoquinoline and pharmaceutically acceptable acid addition salts thereof.

7. The compound of claim 1 which is:
8-Ethoxycarbonylamino-4-p-chloro-phenyl-2-methyl-1,2,3,4-tetrahydro-isoquinoline and pharmaceutically acceptable acid addition salts thereof.

8. The compound of claim 1 which is:
8-Ethoxycarbonylamino-4-p-chloro-phenyl-2-methyl-1,2,3,4-tetrahydro-isoquinoline-hydrochloride.

9. Pharmaceutical compositions having advantageous central nervous system effects as active ingredient an effective amount of at least one compound of the formula I as defined in claim 1 or a pharmaceutically acceptable acid addition salt thereof in admixture with suitable inert non-toxical, pharmaceutical carriers and/or excipients.

* * * * *

UNITED STATES PATENT AND TRADEMARK OFFICE
CERTIFICATE OF CORRECTION

PATENT NO. : 4,537,895
DATED : August 27, 1985
INVENTOR(S) : DEÁK et al.

It is certified that error appears in the above—identified patent and that said Letters Patent is hereby corrected as shown below:

In the cover sheet, the date for the Foreign Application Priority Data should read --June 4, 1982--.

Signed and Sealed this

Fifteenth Day of July 1986

[SEAL]

Attest:

Attesting Officer

DONALD J. QUIGG

Commissioner of Patents and Trademarks